(12) United States Patent
Marek-Trzonkowska et al.

(10) Patent No.: US 11,072,779 B2
(45) Date of Patent: Jul. 27, 2021

(54) METHOD FOR EX VIVO EXPANSION OF REGULATORY T CELLS

(71) Applicant: GDANSKI UNIWERSYTET MEDYCZNY, Gdansk (PL)

(72) Inventors: Natalia Marek-Trzonkowska, Gdansk (PL); Piotr Trzonkowski, Sopot (PL); Malgorzata Mysliwiec, Gdansk (PL)

(73) Assignee: GDANSKI UNIWERSYTET MEDYCZNY, Gdansk (PL)

( * ) Notice: Subject to any disclaimer, the term of this patent is extended or adjusted under 35 U.S.C. 154(b) by 386 days.

(21) Appl. No.: 16/063,144

(22) PCT Filed: Dec. 19, 2016

(86) PCT No.: PCT/PL2016/000152
§ 371 (c)(1),
(2) Date: Jun. 15, 2018

(87) PCT Pub. No.: WO2017/105265
PCT Pub. Date: Jun. 22, 2017

(65) Prior Publication Data
US 2018/0362928 A1  Dec. 20, 2018

(30) Foreign Application Priority Data
Dec. 17, 2015  (PL) .......................................  415351

(51) Int. Cl.
*C12N 5/0783* (2010.01)

(52) U.S. Cl.
CPC ........ *C12N 5/0637* (2013.01); *C12N 2500/00* (2013.01); *C12N 2501/2302* (2013.01); *C12N 2501/51* (2013.01); *C12N 2501/515* (2013.01); *C12N 2501/998* (2013.01); *C12N 2523/00* (2013.01)

(58) Field of Classification Search
CPC .............. C12N 5/0637; C12N 2500/00; C12N 2501/2302; C12N 2523/00
See application file for complete search history.

(56) References Cited

U.S. PATENT DOCUMENTS

2005/0186207 A1* 8/2005 Bluestone ................. A61P 5/50
424/144.1

FOREIGN PATENT DOCUMENTS

| PL | 218400 B1 | 11/2014 |
|---|---|---|
| WO | 2006/090291 A2 | 8/2006 |
| WO | 2010/135255 A1 | 11/2010 |
| WO | 2013/050596 A1 | 4/2013 |
| WO | 2013/109759 A1 | 7/2013 |

OTHER PUBLICATIONS

Stelmaszczyk-Emmel et al. Frequency and Activation of CD4+ CD25 high FoxP3+ Regulatory T Cells in Peripheral Blood from Children with Atopic Allergy. Int Arch Allergy Immunol 2013;162:16-24 (Year: 2013).*
Gu et al. Moderate Hypothermia Inhibits Brain Inflammation and Attenuates Stroke-Induced Immunodepression in Rats. CNS Neuroscience & Therapeutics 20 (2014) 67-75 (Year: 2014).*
Kocaoemer et al. Human AB Serum and Thrombin-Activated Platelet-Rich Plasma Are Suitable Alternatives to Fetal Calf Serum for the Expansion of Mesenchymal Stem Cells from Adipose Tissue. Stem Cells 2007;25:1270-1278 (Year: 2007).*
X-VIVO Media. Lonza, p. 1-3 (Year: 2010).*
International Search Report and Written Opinion dated Mar. 22, 2017, from the corresponding PCT/PL2016/000152, 16 sheets.
Chi-Yen Lin et al: "Enhancing Protein Expression in HEK-293 Cells by Lowering Culture Temperature", PLOS One, vol. 10, No. 4, Apr. 20, 2015 (Apr. 20, 2015), p. e0123562, XP055354395, DOI: 10.1371/journal.pone.0123562, abstract.
K. L. Hippen et al: "Massive ex Vivo Expansion of Human Natural Regulatory T Cells (Tregs) with Minimal Loss of in Vivo Functional Activity", Science Translational Medicine, vol. 3, No. 83, May 18, 2011 (May 18, 2011), pp. 83ra41-83ra41, XP055354389, ISSN: 1946-6234, DOI: 10.1126/scitranslmed.3001809 abstract.
Masteller E L et al: "Antigen-specific regulatory T cells-Ex vivo expansion and therapeutic potential", Seminars in Immunology, W.B. Saunders Company, PA, US, vol. 18, No. 2, Apr. 1, 2006 (Apr. 1, 2006), pp. 103-110, XP024907994, ISSN: 1044-5323, DOI: 10.1016/J.SMIM.2006.01.004 [retrieved on Apr. 1, 2006] p. 104, paragraph 3—p. 106.
Andres A (2005). "Cancer incidence after immunosuppressive treatment following kidney transplantation." Crit Rev Oncol Hematol 56(1): 71-85.
Barbaro MP, Spanevello A, Palladino GP, Salerno FG, Lacedonia D, Carpagnano GE, (2014). "Exhaled matrix metalloproteinase-9 (MMP-9) in different biological phenotypes of asthma." Eur J Intern Med 25(1): 92-96.
Berney T, Secchi A (2009). "Rapamycin in islet transplantation: friend or foe?" Transpl Int 22(2): 153-161.
Bluestone JA, Buckner JH, Fitch M, Gitelman SE, Gupta S, Hellerstein MK, Herold KC, Lares A, Lee MR, Li K, Liu W, Long SA, Masiello LM, Nguyen V, Putnam AL, Rieck M, Sayre PH, Tang Q, (2015). "Type 1 diabetes immunotherapy using polyclonal regulatory T cells." Sci Transl Med 7(315): 315ra189.
Bluestone JA, Trotta E, Xu D, (2015). "The therapeutic potential of regulatory T cells for the treatment of autoimmune disease." Expert Opin Ther Targets 19(8): 1091-1103.

(Continued)

*Primary Examiner* — Taeyoon Kim
(74) *Attorney, Agent, or Firm* — Katten Muchin Rosenman LLP

(57) ABSTRACT

The invention relates to a new method for in vitro expansion of CD4+CD25$^{High}$CD127-$^{/LOW}$foxP3+Tregs, wherein the process of Treg expansion takes place permanently or temporarily at a temperature below 37° C., optimally at a temperature of 33° C., the isolated Tregs are expanded in SCGM or X-vivo-20 medium supplemented with human serum or with foetal bovine serum, and magnetic beads coated with anti-CD3 and anti-CD28 antibodies at 1:1 (cell:bead) ratio and interleukin-2 are added to the culture.

5 Claims, 10 Drawing Sheets

(56) References Cited

OTHER PUBLICATIONS

Braza F, Dugast E, Panov I, Paul C, Vogt K, Pallier A, Chesneau M, Baron D, Guerif P, Lei H, Laplaud DA, Volk HD, Degauque N, Giral M, Soulillou JP, Sawitzki B, Brouard S, (2015). "Central role of CD45RA—Foxp3hi memory regulatory T cells in clincal kidney transplantation tolerance." J Am Soc Nephrol 26(8): 1795-1805.
Di Ianni M, Falzetti F, Carotti A, Terenzi A, Castellino F, Bonifacio E, Del Papa B, Zei T, Ostini RI, Cecchini D, Aloisi T, Perruccio K, Ruggeri L, Balucani C, Pierini A, Sportoletti P, Aristei C, Falini B, Reisner Y, Velardi A, Aversa F, Martelli MF, (2011). "Tregs prevent GVHD and promote immune reconstitution in HLA-haploidentical transplantation." Blood 117(14): 3921-398.
Fontenot JD, Gavin MA, Rudensky AY, (2003). "Foxp3 programs the development and function of CD4+CD25+ regulatory T cells." Nat Immunol 4(4): 330-336.
Gambineri E, Torgerson TR, Ochs HD, (2003). "Immune dysregulation, polyendocrinopathy, enteropathy, and X-linked inheritance (IPEX), a syndrome of systemic autoimmunity caused by mutations of FOXP3, a critical regulator of T-cell homeostasis." Curr Opin Rheumatol 15: 430-435.
Gupta S, (2012). "Immunotherapies in diabetes mellitus type 1." Med Clin North Am 96(3): 621-634.
Hoffmann P, Boeld TJ, Eder R, Huehn J, Floess S, Wieczorek G, Olek S, Dietmaier W, Andreesen R, Edinger M, (2009). "Loss of FOXP3 expression in natural human CD4+CD25+ regulatory T cells upon repetitive in vitro stimulation." Eur J Immunol 39(4): 1088-1097.
Kehrmann J, Tatura R, Zeschnigk M, Probst-Kepper M, Geffers R. Steinmann J, Buer J, (2014). "Impact of 5-aza-2'-deoxycytidine and epigallocatechin-3-gallate for induction of human regulatory T cells." Immunology 142(3): 384-395.
Lima XT, Cintra ML, Piaza AC, Mamoni RL, Oliveira RT, Magalhaes RF, Blotta MH, (2015). "Frequency and characteristics of circulating CD4(+) CD28(null) T cells in patients with psoriasis." Br J Dermatol 173 (4): 998-1005.
Malek TR (2003). "The main function of IL-2 is to promote the development of T regulatory cells." J Leukoc Biol 74 (6): 961-965.
Malek TR, Castro I (2010). "Interleukin-2 receptor signaling: at the interface between tolerance and immunity."Immunity 33(2): 153-165.
Marek-Trzonkowska N, Mysliwiec M, Dobyszuk A, Grabowska M, Techmanska I, Juscinska J, Wujtewicz MA, Witkowski P, Mlynarski W, Balcerska A, Mysliwska J, Trzonkowski P, (2012). "Administration of CD4+CD25highCD127—regulatory T cells preserves β-cell function in type 1 diabetes in children." Diabetes Care 35(9): 1817-1820.
Marek-Trzonkowska N, Mysliwec M, Siebert J, Trzonkowski P, (2013). "Clinical application of regulatory T cells in type 1 diabetes." Pediatr Diabetes 14(5): 322-332.
Marek-Trzonkowska N, Mysliwiec M, Dobyszuk A, Grabowska M, Derkowska I, Juscinska J, Owczuk R. Szadkowska A, Witkowski P, Mlynarski W, Jarosz-Chobot P, Bossowski A, Siebert J, Trzonkowski P, (2014). "Therapy of type 1 diabetes with CD4(+) CD25(high)CD127—regulatory T cells prolongs survival of pancreatic islets—results of one year follow-up." Clin Immunol 153(1): 23-30.
Marek N, Bieniaszewska M, Krzystyniak A, Juscinska J, Mysliwska J, Witkowski P, Hellmann A, Trzonkowski P, (2011). "The time is crucial for ex vivo expansion of T regulatory cells for therapy." Cell Translplant 20 (11-12): 1747-1758.
Martelli MF, Di Ianni M, Ruggeri L, Falzetti F, Carotti A, Terenzi A, Pierini A, Massei MS, Amico L, Urbani E, Del Papa B, Zei T, Iacucci Ostini R, Cecchini D, Tognellini R, Reisner Y, Aversa F, Falini B, Velardi A, (2014). "HLA-haploidentical transplantation with regulatory and conventional T-cell adoptive immunotherapy prevents acute leukemia relapse." Blood 124(4): 638-644.

Mu Q, Zhang H, Luo XM, (2015). "SLE: another autoimmune disorder influenced by microbes and diet?" Front Immunol 6(artykul 608): 1-10.
Orent W, McHenry AR, Rao DA, White C, Klein HU, Bassil R, Srivastava G, Replogle JM, Raj T, Frangieh M, Cimpean M, Cuerdon N, Chibnik L,Khoury SJ, Karlson EW, Brenner MB, De Jager P, Bradshaw EM, Elyaman W, (2015). "Rheumatoid arthritis-associated RBPJ polymorphism alters memory CD4+ T cells." Hum Mol Genet DOI: 10.1093/hmg/ddv474(in press).
Panettieri RA, Jr Covar R, Grant E, Hillyer EV, Bacharier L, (2008). "Natural history of asthma: persistence versus progression—does the beginning predict the end?" J Allergy Clin Immunol 121(3): 607-613.
Polansky JK, Kretschmer K, Freyer J, Floess S, Garbe A, Baron U, Olek S, Hamann A, von Boehmer H, Huehn J. (2008). "DNA methylation controls Foxp3 gene expression." Eur J Immunol 38(6): 1654-1663.
Prokai A, Csohany R, Sziksz E, Pap D, Balicza-Himer L, Boros S, Magda B Vannay A, Kis-Petik K, Fekete A, Peti-Peterdi J, Szabo Aj, [2015]. "Calcineurin-inhibition results in upregulation of local renin and subsequent vascular endothelial groth factor production in renal collecting ducts." Transplantation DOI: 10.1097/TP.0000000000000961 (in press).
Pujol-Autonell I, Ampudia RM, Monge P, Lucas AM, Carrascal J, Verdaguer J, Vives-Pi M, (2013). "Immunotherapy with Tolerogenic Dendritic Cells Alone or in Combination with Rapamycin Does Not Reverse Diabetes in NOD Mice." ISRN Endocrinol 2013(ID 346987): 1-5.
Rama I, Grinyo JM (2010). "Malignancy after renal transplantation: the role of immunosuppression." Nat Rev Nephrol 6 (9): 511-519.
Ryba M, Marek N, Hak L, Rybarczyk-Kapturska K, Mysliwiec M, Trzonkowski P, Mysliwska J, (2011). "Anti-TNF rescue CD4+ Foxp3+ regulatory T cells in patients with type 1 diabetes from effects mediated by TNF." Cytokine 55(3): 353-361.
Senecal V, Deblois G, Beauseigle D, Schneider R, Brandenburg J, Newcombe J, Moore CS, Prat A, Antel J, Arbour N, (2015). "Production of IL-27 in multiple sclerosis lesions by astrocytes and myeloid cells: Modulation of local immune responses." Glia DOI: 10.1002/glia.22948 (in press).
Tang Q, Bluestone JA (2013). "Regulatory T-cell therapy in transplantation-moving to the clinic." Cold Spring Harb Perspect Med 3(11): pii: a015552.
Trzonkowski P, Bacchetta R, Battaglia M, Berglund D, Bohnenkamp HR, ten Brinke A, Bushell A, Cools N, Geissler EK, Gregori S, Marieke van Ham S, Hilkens C, Hutchinson JA, Lombardi G, Madrigal JA, Marek-Trzonkowska N, Martinez-Caceres EM, Roncarolo MG, Sanchez-Ramon S, Saudemont A, Sawitzki B, (2015). "Hurdles in therapy with regulatory T cells." Sci Transl Med 7(304): 304ps18.
Trzonkowski P, Bieniaszewska M, Jusciiiska J, Dobyszuk A, Krzystyniak A, Marek N, Mysliwska J, Hellmann A, (2009). "First-in-man clinical results of the treatment of patients with graft versus host disease with human ex vivo expanded CD4+CD25+CD127—T regulatory cells." Clin Immunol 133(1): 22-26.
Trzonkowski P, Dukat-Mazurek A, Bieniaszewska M, Marek-Trzonkowska N, Dobyszuk A, Jusciiiska J, Dutka M, Mysliwska J, Hellmann A, (2013). "Treatment of graft-versus-host disease with naturally occurring T regulatory cells." BioDrugs 27(6): 605-614.
Trzonkowski P, Szaryiiska M, Mysliwska J, Mysliwski A, (2009). "Ex vivo expansion of CD4(+)CD25(+) T regulatory cells for immunosuppressive therapy." Cytometry A 75(3): 175-188.
Vignali DA, Collison LW, Workman CJ, (2008). "How regulatory T cells work" Nat Rev Immunol 8(7): 523-532.
Wang YM, Zhang GY, Wang Y, Hu M, Wu H, Watson D, Hori S, Alexander IE, Harris DC, Alexander SI, (2006). "Foxp3-transduced polyclonal regulatory T cells protect against chronic renal injury from adriamycin." J Am Soc Nephrol 17(3): 697-706.
Yi S, Ji M, Wu J, Ma X, Phillips P, Hawthorne WJ, O'Connell PJ, (2012). "Adoptive transfer with in vitro expanded human regulatory T cells protects against porcine islet xenograft rejection via interleukin-10 in humanized mice." Diabetes 61(5): 1180-1191.

(56) References Cited

OTHER PUBLICATIONS

Zhang N, Su D, Qu S, Tse T, Bottino R, Balamurugan AN, Xu J, Bromberg JS, Dong HH, (2006). "Sirolimus is associated with reduced islet engraftment and impaired beta-cell function." Diabetes 55(9): 2429-2436.

Zhao K, Ruan S, Yin L, Zhao D, Chen C, Pan B, Zeng L, Li Z, Xu K, (2015). "Dynamic regulation of effector IFN-y-producing and IL-17-producing T cell subsets in the development of acute graft-versus-host disease." Mol Med Rep DOI: 10.3892/mmr.2015.4638(in press).

* cited by examiner

METHOD FOR EX VIVO EXPANSION OF REGULATORY T CELLS

CLAIM OF PRIORITY

This application is a § 371 national stage of the PCT International Application No. PCT/PL2016/000152, filed on Dec. 19, 2016, which claims priority of Polish Application No. P.415351, filed Dec. 17, 2015, the entire contents of which are hereby incorporated by reference into this application.

FIELD OF THE INVENTION

The invention relates to the method of ex vivo expansion of regulatory T cells (Tregs) for their clinical use in immunotherapy. Tregs produced in this way are suitable for treatment of autoimmune diseases, including e.g. multiple sclerosis, rheumatoid arthritis, type 1 diabetes mellitus, and for suppression of adverse immune responses, such as graft rejection, allergic reactions and graft versus host disease (GVHD).

BACKGROUND OF THE INVENTION

Tregs account for ≈1% of peripheral blood lymphocytes but play an important role in maintaining self-tolerance (Trzonkowski P, 2009) (Vignali D A, 2008) (Yi S, 2012). Lack of Tregs leads to development of multiple autoimmune diseases and hypersensitivities, as it is observed in patients with immune dysregulation, polyendocrinopathy, enteropathy, X-linked syndrome (IPEX) (Gambineri E, 2003). Tregs can be called "intelligent steroids", as like steroids they inhibit inflammatory responses and are immunosuppressive but in contrast to the drugs the physiological suppressor activity of Tregs affects only pathological reactions (e.g. those directed against self-tissues). Results of clinical trials in which Tregs were used—including our observations—indicate that Treg treatment is safe and does not impair immune responses to foreign and dangerous antigens (viruses, bacteria, tumour cells) (Marek-Trzonkowska N, 2012) (Marek-Trzonkowska N. 2014) (Martelli M F, 2014) (Bluestone J A, 2015).

Our research team has been investigating the biology and clinical application of Treg cells for more than 10 years. We were the first who have used in vitro expanded Tregs for the treatment of graft versus host disease (GVHD) in adults (NKEBN/458-310/2008) (Trzonkowski P, 2009) (Trzonkowski P, 2013), then in type 1 diabetes mellitus (T1DM) in children (TregVAC ISRCTN06128462; TregVAC2.0EudraCT:2014-004319-35) (Marek-Trzonkowska N, 2012) (Marek-Trzonkowska N, 2014), and subsequently for the treatment of multiple sclerosis (TregSM EudraCT:2014-004320-22) (Trzonkowski P, 2015).

Currently, trials on clinical application of Tregs have been conducting in multiple medical centres all over the world and they focus on treatment/prevention of GVHD (e.g. Treg002EudraCT:2012-002685-12) (Di Ianni M, 2011), treatment of T1DM in adults (NCT01210664), tolerance induction in kidney recipients (e.g. NCT02091232 and NCT02129881) and in liver transplantation (ThRIL NCT02166177 and NCT01624077) (Trzonkowski P, 2015).

A dynamic sprout of Treg based therapies has been observed during the last years. All these projects share a common goal, namely intelligent immunosuppression that would allow to inhibit adverse immune reactions without impairing the physiological immune response. All these research projects have also been struggling with the same technical problems associated with Treg isolation and culture. The first of these issues was the low purity of isolated population, that affected safety and efficacy of the treatment (Trzonkowski P, 2009) (Tang Q, 2013). The hurdle was eventually solved by introduction of a cell sorter for Treg isolation, as described in the patent PL 218400 B. Nevertheless, none of the known methods for Treg expansion is able to provide their extensive proliferation without loss of characteristic Treg phenotype, particularly, the high expression of FoxP3 for entire culture duration (10-14 days). Each time, even if the culture is conducted according to standards of Good Manufacturing Practice (GMP), a significant decline in the percentage of FoxP3$^+$ cells is observed in the second week of Treg expansion. In addition, the cells start to produce proinflammatory cytokines, including interferon γ (IFN-γ). Altogether, these changes decrease immunosuppressive activity of Tregs, directly affecting their function and are responsible for diminished efficacy of Treg based therapies (Marek N, 2011) (Hoffmann P, 2009) (Tang Q, 2013).

WO 2013/050596 A1 patent describes a method for in vitro expansion of Tregs in the presence of rapamycin that is an mTOR (mammalian target for rapamycin) kinase inhibitor, suberoylanilide hydroxamic acid (vorinostat) an inhibitor of histone deacetylase and azacitidine an inhibitor of DNA methylation. It has been shown that a relative Treg stability can only be achieved when combination of all these three compounds is used simultaneously. Nevertheless, supplementation of Treg cultures with the chemotherapeutics did not completely prevent the decrease in FoxP3 expression during culture and already after 7 days the percentage of FoxP3$^+$ cells dropped below 90%. In addition, each of these compounds is known to reduce Treg viability and proliferative potential.

Patent WO 2010/135255 A1 disclosed a method for ex vivo expansion of CD4$^+$CD25$^+$ Tregs that during 3 weeks resulted in 100- to 1000-fold increase in the initial Treg number, while for 14-day period the values ranged from 60 to 500. In addition, the magnetic methods of Treg isolation described in this patent resulted in low initial Treg purity (40-75% on day 0), thus consequently a percentage of FoxP3$^+$ cells in the second week of the culture on average was equal to 40-50%.

WO 2006/090291 patent describes a method of Treg expansion in the presence of rapamycin. Supplementation of Treg culture with the chemotherapeutic was aimed to inhibit proliferation of effector T cells (Teffs) that could be present in the culture as contamination. The fold increase of CD4$^+$CD25$^+$ cell number after 14-day culture with rapamycin presented in the patent was lower than 20, while after 21 days did not exceed 40.

None of the known inventions or scientific publications describe Treg cell cultures at temperatures below 37° C. The method of Treg expansion provided by the present invention is the first that introduces change in Treg culture temperature to achieve a significantly higher number of cells without simultaneous decrease in their quality and suppressor activity. All patented methods of Treg expansion have been exclusively used the temperature of 37° C. Our team is the first who has tested temperatures below 37° C. in Treg cultures, demonstrating that 33° C. allows to obtain more than 3-fold higher number of Tregs in a given unit of time as compared with the cultures at the standard temperature (i.e. 37° C.).

Elaboration of a safe, simple to implement and economical method for expansion of stable Tregs characterised with high FoxP3 expression and a potent suppressor activity is of key importance for advancement and success of clinical trials utilising Tregs as a therapeutic tool. Ability to regulate the immune response is important from the therapeutic point of view. Physiologically, the immune system recognises and destroys foreign and dangerous antigens, and tolerates self-tissues. Nevertheless, in autoimmune diseases, such as multiple sclerosis (MS), type 1 diabetes mellitus (T1DM), psoriasis, systemic lupus erythematosus (SLE) or rheumatoid arthritis (RA), this mechanism is impaired (Sénécal V, 2015) (Trzonkowski P, 2015) (Marek-Trzonkowska N, 2012) (Pujol-Autonell I, 2013) (Lima X T, 2015) (Mu Q, 2015) (Orent W, 2015). The immune system begins to destroy the patient's own tissues and organs, leading to irreversible changes. The current management of autoimmune diseases commonly involves nonantigen-specific immunosuppression and inhibition of inflammatory response. However, this treatment emerges ineffective in long time perspective. Despite the initial improvement, progression of the disease cannot be completely stopped, and discontinuation of the treatment usually results in an exacerbation of the symptoms. Moreover, this treatment is associated with compromised immunity (Gupta S, 2012). Therefore, the patients become susceptible to various infections, which have much more severe manifestation, than in healthy individuals who are not treated with immunosuppressive drugs. Furthermore, non-specific immunosuppression increases the risk of cancer (higher prevalence of cancer in patients receiving immunosuppressants) (Andrés A, 2005) (Rama 1, 2010).

Regulation of the immune response is also an important issue from the viewpoint of transplantation medicine. Organ transplantation is usually a life-saving procedure but is also associated with life-long treatment with potent immunosuppressive drugs. Discontinuation of this treatment results in increased immune response to the graft tissues, which leads to rapid graft loss. The use of immunosuppressive drugs, as in therapy of autoimmune diseases, is associated with the risk of severe adverse effects. Furthermore, some of these drugs simultaneously protect the transplanted organ from the recipient immune system and are toxic for the graft or other tissues. Examples include nephrotoxic inhibitors of calcineurin (ciclosporin and tacrolimus) used in kidney transplantation (Prókai Á, 2015) or rapamycin used in pancreatic islet recipients despite its deleterious impact on transplanted β cell function (Zhang N, 2006) (Berney T 2009).

The problem of immunosuppression and regulation the of immune response is also closely associated with bone marrow transplantation. The principal difference between organ and bone marrow transplantation is that in the former case, medicine intends to protect the transplanted organ from the destructive action of the recipient's immune system, while in the latter case, there is no risk of transplant rejection but the transplanted bone marrow is a source of cells that attack the recipient's body and may lead to death (Di Ianni M, 2011) (Zhao K, 2015). However, regardless of the origin of the immune cells attacking the patient's body, currently the fight against the excessive immune response come down to using non-specific immunosuppression.

An apparently different issue is the excessive immune response to innocuous foreign antigens, as it is observed in various types of hypersensitivities that all together are colloquially called allergies. Most of these disorders can be successfully treated symptomatically with the available medications. Nevertheless, in case of asthma the problem is more complex. The disease progresses with time, inflammation exaggerates leading to persistent structural changes in the airways and medical treatment become ineffective (Panettieri R A Jr, 2008) (Barbaro M P, 2014).

To summarize, fully effective and safe drugs used for treatment of autoimmune and allergic diseases, as well as in transplant recipients would be those that target directly the mechanisms responsible for the disease onset/injury of the transplanted organ and at the same time would not impair the physiological immune response to foreign and dangerous antigens. A chance for so-called intelligent immunosuppression is offered by Tregs. However, the success of clinical therapy with Tregs depends on elaboration of the optimal protocol of their expansion that will guarantee safety and will result with high numbers of stable and suppressive Tregs for entire culture duration (Tang Q, 2013).

The method described in this patent application meets the above listed criteria and may be successfully used for the expansion of both polyclonal and antigen-specific Tregs.

SUMMARY OF THE INVENTION

Decreasing the temperature of Treg expansion below 37° C., particularly setting culture temperature at 33° C., significantly improves the quality and stability of these cells. Treg cells expanded at 33° C. are characterised by a constant and high expression of FoxP3 and α subunit of the IL-2 receptor (CD25), as well as demethylation of Treg-specific demethylated region (TSDR) of FoxP3 gene which is associated with a higher suppressor activity and proliferative potential of these cells.

Until now, the main problem in Treg culture has been their low proliferative potential and decline in frequency of FoxP3$^+$ cells over time (Marek N, 2011) (Hoffmann P, 2009) (Tang Q, 2013). Changing just the culture temperature, we have managed to eliminate these two problems. Culture at 33° C. enables to obtain a several-fold higher number of Tregs within 14 days (FIG. 1) that are characterized with highly demethylated TSDRs (FIG. 12) and greater expression of FoxP3 (FIG. 2), than methods using the standard temperature of expansion, i.e. 37° C.

Consequently, the technique described in the patent allows to decrease the duration of Treg expansion and thus to treat more patients within the same time, concomitantly preserving higher quality/stability of the expanded cells (FIG. 3 and FIG. 12). The high proliferative potential of Tregs at 33° C. is at least partially associated with a higher (FIG. 4) and more stable (FIG. 5) expression of CD25 molecule on the surface of these cells (a higher percentage of CD25$^{High}$ cells and a higher intensity of CD25 molecule production over time). CD25 is a subunit of high affinity receptor for interleukin-2 (IL-2), a cytokine that is a mitogen of all T cells and is essential for generation, proliferation and function of Tregs (Malek T R, 2003) (Malek T R, 2010). Among three subunits (α, β and γ) that comprise the high-affinity IL-2 receptor, we only determined the expression of the α chain (CD25), as it is one of the most important and commonly accepted Treg markers. Nevertheless, we may assume that decrease in the culture temperature to 33° C. not only increased expression of the CD25 but also upregulated the remaining subunits of the IL-2 receptor, leading to higher IL-2 sensitivity and robust proliferation of Tregs expanded at 33° C.

Noteworthy is also the fact that Tregs expanded at 33° C. are characterised by a significantly higher frequency of cells with the highest intensity of FoxP3 expression (FoxP3$^{High}$) for the entire culture duration as compared with those at 37°

C. (FIG. 6). Furthermore, FoxP3$^{High}$ population reveals significantly higher production of CD25 (FIG. 7) and stability of FoxP3 expression (FIG. 8) over time at 33° C., than FoxP3$^{High}$ cells expanded at a temperature of 37° C.

Noteworthy, it is known that FoxP3$^{High}$ cells are a Treg fraction with the highest suppressive potential, as immunoregulatory activity of Tregs is in positive correlation with the intensity of FoxP3 expression (Marek N, 2011) (Ryba M, 2011). Thus, a high percentage of FoxP3$^{High}$ cells guarantees a higher efficacy of a Treg based therapy. In the functional tests that we performed the impact of Tregs on proliferation of CD4$^+$ Teffs and production of interferon γ (IFN-γ) by these cells was analysed. Our results indicate that Tregs expanded at 33° C. are more potent inhibitors of Teff proliferation and exhibit tendency towards stronger suppression of IFN-γ production by these cells, as compared with Tregs cultured at a temperature of 37° C. (FIGS. 9-10). Furthermore, in contrast to Tregs cultured at 37° C., cells expanded at 33° C. produced only traceable amounts of IFN-γ during a 14-day culture (FIG. 11). It should be borne in mind that Tregs use multiple other mechanisms crucial for tolerance induction which have not been analysed in our study. One of them is inhibition of dendritic cell (DC) maturation, leading to generation of tolerogenic DCs. In addition, a direct Treg-DC contact induces expression of indolamine 2,3-dioxygenase (IDO) in DCs which catalyses degradation of tryptophan, thereby inhibiting the proliferation of activated cytotoxic and helper T cells (Tc and Th cells, respectively) (Vignali D A, 2008) (Marek-Trzonkowska N, 2013). In our experimental model, we did not use dendritic cells. Therefore, the above mechanism could not be verified. Any approach to assess the functional potential of Tregs in vitro has always a number of limitations. Therefore, the real extent of functional superiority of Tregs expanded at 33° C. over those at 37° C. can only be fully verified in in vivo experiments. Nevertheless, for many years, scientists have constantly concluded that the gene encoding FoxP3 transcription factor is the major regulator of Treg development and function. Transfer of just this single gene into conventional, naive T cells was found to provide Treg phenotype and some regulatory functions (Wang Y M, 2006) (Fontenot J D, 2003). As natural Tregs, such modified lymphocytes produced barely detectable amounts of proinflammatory cytokines, expressed Treg surface markers (e.g. CTLA-4), and inhibited Teff proliferation in FoxP3 expression dependent manner. In conclusion, there is a strong positive correlation between a high expression of FoxP3 and a potent suppressor activity of Tregs (Wang Y M, 2006) (Fontenot J D, 2003; Marek N, 2011) (Ryba M, 2011). Recent studies showed that FoxP3 expression and Treg function are regulated by epigenetic status of the Foxp3 gene locus. It has been demonstrated that natural Tregs are characterized by specific DNA demethylation at TSDR of FoxP3 gene (Polansky J K 2008) (Hoffmann 2009) (Braza F 2015). Nevertheless, it was also reported that during expansion in vitro TSDRs undergo methylation even in natural Tregs. This phenomenon was accompanied with continuous decrease in suppressive activity of Tregs and increasing production of proinflammatory cytokines (e.g IL-2 and IFN-γ) (Hoffmann 2009). However, decreasing temperature of Treg culture to 33° C. we prevented methylation of TSDR and kept the cells stable for entire duration of the culture (FIG. 12). Multiple teams have been looking for years for methods that could prevent TSDR methylation and continuous loss of FoxP3 expression in vitro. Use of DNA demethylation agents is a potential option. However, our previous experience with 5-Aza-2'-deoxycytydine (AZA) suggests that epigenetic modification of TSDR is a precisely regulated process that cannot be easily mimicked in vitro. In addition, we found lower cell viability and proliferation when Tregs were cultured with AZA. Similar results presented Kehrmann et al. who found that despite AZA induced TSDR hypomethylation, it also reduced cell proliferation (Kehrmann L 2014). While temperature of 33° C. not only prevents TSDR methylation, but also enhances Treg expansion.

Our study showed that 33° C. is the optimal temperature for Treg culture. However, further decrease of culture temperature is not recommended, as it inhibits the intensity of cell proliferation. The lower limit of temperature at which Tregs maintain their viability for at least 14 days is 29° C. However, under these conditions, an almost complete inhibition of Treg expansion occurs and the cells lose their characteristic phenotype (FIG. 13-14). As for all living organisms and cells, the temperature tolerance for Tregs is also strictly defined. Surprisingly—to the current state of the art—our observations showed that the optimal temperature for Treg culture is below the physiological temperature of the human body, namely at 33° C.

The present invention relates to a method of in vitro expansion of CD4$^+$CD25$^{High}$CD127$^{-/Low}$FoxP3$^+$ Tregs, wherein The process of Treg expansion takes place permanently or temporarily at a temperature below 37° C.

The isolated Tregs are expanded in SCGM or X-vivo-20 medium supplemented with human serum or foetal bovine serum.

Magnetic beads coated with anti-CD3 and anti-CD28 antibodies at a 1:1 cell:bead ratio and interleukin-2 are added to the culture.

A method wherein Treg expansion take place optimally at a temperature of 33° C.

A method wherein Tregs proliferate intensively and preserve their full phenotype.

A method that provides constant and high expression of FoxP3, and α subunit of IL-2 receptor (CD25), as well as prevents TSDR methylation.

A method that allows to use the generated Tregs for clinical therapies of adverse immune reactions.

A method wherein Tregs are polyclonal and/or antigen-specific cells.

A method wherein adverse immune reactions are defined as: autoimmune diseases, transplant rejection, allergic reactions and graft-versus-host disease.

The advantages of the present invention are as follows:
(1) a higher number of Tregs obtained during a 14-day culture, than with the known methods of Treg expansion that do not implement other cell types to the Treg culture and are applicable for clinical use and (FIG. 1)
(2) in the case of clinical application, the method enables the following:

reduction of the time for cell production, and thus the treatment can be provided to higher number of patients and/or to obtain ≈300% higher number of Tregs within a specified period, which will allow to increase the therapeutic dose of Tregs that affects the treatment efficacy and/or to expand the therapeutically significant number of Tregs after drawing of <250 ml of blood, making Treg therapy available for the treatment of the youngest children, when collection of a large blood volume is infeasible.

(3) very high stability of Tregs during the culture; significantly higher expression of FoxP3 (FIGS. 3 and 8) and CD25 molecule (FIG. 5), as well as higher % of cells with demethylated TSDRs (FIG. 12) for entire duration of expansion, as compared with Tregs cultured at 37° C. or in the case of culture supplementation with chemotherapeutics (e.g. rapamycin) that are intended to preserve Treg stability; in contrast to the chemotherapeutics, the culture temperature of 33° C. does not impair Treg viability, is not cytotoxic and does not put the patient safety at risk.

(4) over entire culture duration Tregs expanded at 33° C. are characterised by a significantly higher percentage of FoxP3$^{High}$ cells (FIG. 6), that are more stable as compared with Tregs simultaneously expanded at temperature of 37° C. (FIG. 8), which exerts a beneficial impact on efficacy of Treg based cellular therapies.

(5) Tregs expanded at a temperature of 33° C., produce only traceable amounts of JFN-γ (a proinflammatory cytokine) over entire culture duration (approximately 2% of IFN-γ$^+$ cells), while expansion at a temperature of 37° C. is associated with a gradual increase in the percentage of Treg IFN-γ$^+$ cells and is about 2.5-fold higher on day 14 of the culture (FIG. 11) (Marek N, 2011).

(6) as compared to Tregs expanded at the standard temperature of 37° C., the cells cultured at 33° C. are more potent inhibitors of Teff proliferation (FIG. 9) and show a tendency towards a stronger suppression of IFN-γ production by these cells (FIG. 10)—this phenomenon is of importance for efficacy of Treg based therapies.

(7) the high replicability of the results for Tregs expanded at 33° C. without regard to donor characteristic including gender and age, guarantees, inter alia, a higher predictability of the manufacturing process and therapeutic effect of Tregs in future clinical trials.

(8) the method is not associated with risk of adverse effects that can potentially occur when Treg cultures are supplemented with chemical compounds/drugs/other cells in aim to improve the cell stability or proliferation.

(9) as compared to the previously described techniques for Treg expansion, our method
    requires neither additional funding nor additional labour in aim to improve Treg quality and quantity.

Figure 1:
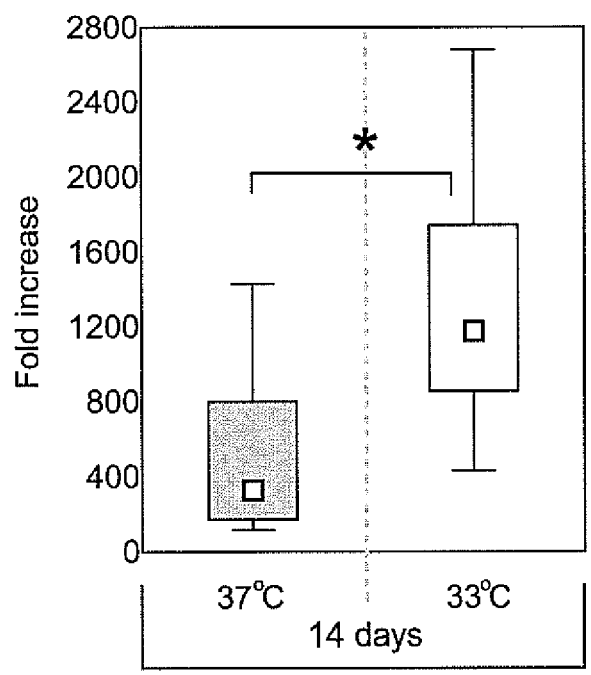
FIG. 1—presents fold increase of the initial Treg number after 14-day culture. The figure depicts a comparison of fold increase of Treg number after 14-days expansion at standard temperature of 37° C. (grey bar; n=8) and at 33° C. (white bar; n=8). This parameter was calculated as a ratio of the final cell number on day 14 of expansion under a given culture condition to the initial cell number. Hence, the values are usually not whole numbers (the results are given with an accuracy to two decimal places). The differences were calculated with Mann-Whitney test for non-parametric data. The values are shown as median, minimum and maximum. An asterisk indicates statistical significance (p<0.05).

The present invention is illustrated by the following example, which is not its limitation

EXAMPLE

Isolation of Tregs and CD4$^+$ Teffs

Peripheral blood Tregs and CD4$^+$ Teffs were isolated from buffy coats derived from female and male volunteer blood donors. First, peripheral blood mononuclear cells (PBMC) were obtained by Ficoll/Uropoline gradient centrifugation. Then, CD4$^+$ T cells were isolated with negative immunomagnetic selection (isolation purity 90-99%). For this purpose, the EasySep Human CD4+ T Cell Enrichment Kit (Stemcell Technologies) was used. The kit depletes the samples from cells expressing the following antigens: CD8, CD14, CD16, CD19, CD20, CD36, CD56, CD66b, CD123, TCRγ/δ and glycophorin A. Subsequently, the isolated CD4$^+$ T cells were labeled with monoclonal antibodies (mAb, 5 μl mAB/10$^6$ cells) specific for the following antigens: CD3, CD4, CD25, CD127, CD8, CD19, CD16 and CD14 (BD Biosciences). The last 4 mAbs were conjugated with the same fluorochrome in aim to minimize the fluorescence overlap and cut-off in one step cytotoxic T cells (Tc), B cells, natural killer (NK) cells and monocytes, respectively. These cells were defined all together in sorting algorithm as lineage.

Then, cells were sorted with FACS sorter into the following phenotype of Tregs: CD3$^+$CD4$^+$CD25$^{high}$CD127$^{-/Low}$doublet$^-$lineage$^-$dead$^-$ and Teffs: CD3$^+$CD4$^+$CD25$^-$CD127$^{High}$doublet$^-$lineage$^-$dead$^-$. The post-sort purity of Tregs was ~100% [median(min−max): 98%(97−99)]. It should be underlined that the cell sorter Influx (BD Biosciences) that was used for Treg isolation is a GMP (Good Manufacturing Practice) adapted machine. Its considerable advantage from the viewpoint of clinical therapy is the replaceable sample line, which eliminates the risk of cross contamination. However, depending on the application (research study/clinical therapy), Tregs can also be obtained with other types of cell sorter. The isolation algorithm described here and the method for Treg expansion according to the present invention, allows to replicate the results of Treg expansion also when different model of cell sorter is used. Therefore, the cell sorter used in this example is not a limitation of the present invention.

The isolated Tregs and Teffs were then seeded into separate plates and expanded at 37° C. and at 33° C. in SCGM culture medium (CellGro) which meets GMP criteria. The medium contained antibiotics (penicillin 100 U/ml and streptomycin 100 mg/ml) and was supplemented with human inactivated serum AB (10%) and interleukin-2 (IL-2; 2000 U/ml; Proleukin; Chiron, San Diego, Calif.). On the day 0 and day 7 of the culture, magnetic beads coated with anti-CD3 and anti-CD28 antibodies (Invitrogen; Carlsbad, Calif.) were added to the culture at a 1:1 cell:bead ratio. The beads mimic stimulation by antigen-presenting cells and thus induce Treg proliferation. In some cultures, a Treg sample was also expanded at 29° C. to determine the lower temperature limit at which Tregs keep their viability, proliferative potential and characteristic phenotype.

Fold Increase of Initial Treg Number after 14-Day Culture

After 14 days, the Tregs were harvested and washed with a PBS, beads were removed and cells were counted. The fold increase of Treg number was calculated as a ratio of the final cell number on day 14 of expansion under a given culture condition to the initial cell count. It was observed that 14-day culture of Tregs at 33° C. resulted in ≈3-fold higher cell counts as compared with Tregs expanded at 37° C. (FIG. 1). It was also found that 29° C. is the lower limit of temperature at which Tregs keep their viability. However, Treg proliferation was suppressed at this temperature. Therefore, a decrease in culture temperature below 33° C. is not recommended, and 33° C. is the optimal temperature for Treg culture.

Prolongation of the culture to 4-5 weeks significantly reduced the percentage of FoxP3$^+$ cells when they were expanded at 37° C. (≈40-45% of FoxP3$^+$ cells), while Tregs cultured at 33° C. were constantly characterised by high FoxP3 expression (≈90-95% of FoxP3$^+$ cells) and intensive proliferation. After 4 and 5 weeks of the culture, Tregs expanded at 33° C. revealed an ≈6000- and 115000-fold increase, respectively. Therefore, prolongation of Treg culture at 33° C. is feasible and results with several-fold higher number of stable cells of high quality. Nevertheless, the decision regarding duration of Treg culture depends on the application. In clinical treatment, a 7-14 day-expansion is sufficient to obtain a therapeutically relevant number of Tregs (Marek-Trzonkowska N, 2012) (Marek-Trzonkowska N, 2014). The cultures at 29° C. had to be ceased after 3 weeks due to the low cell viability and inhibition of their proliferation.

Phenotype Control

On each 7 and 14 day of the culture, samples of Tregs expanded at 33° C., 37° C. and 29° C. were collected and labelled with the following monoclonal antibodies: anti-CD3, anti-CD4, anti-CD25, anti-CD127, anti-CD62L, anti-CD45RA and anti-FoxP3, using the Foxp3 Staining Buffer Set (eBiosciences). Then, the cells were analysed with flow cytometer (Canto II, BD Biosciences).

Figure 2:
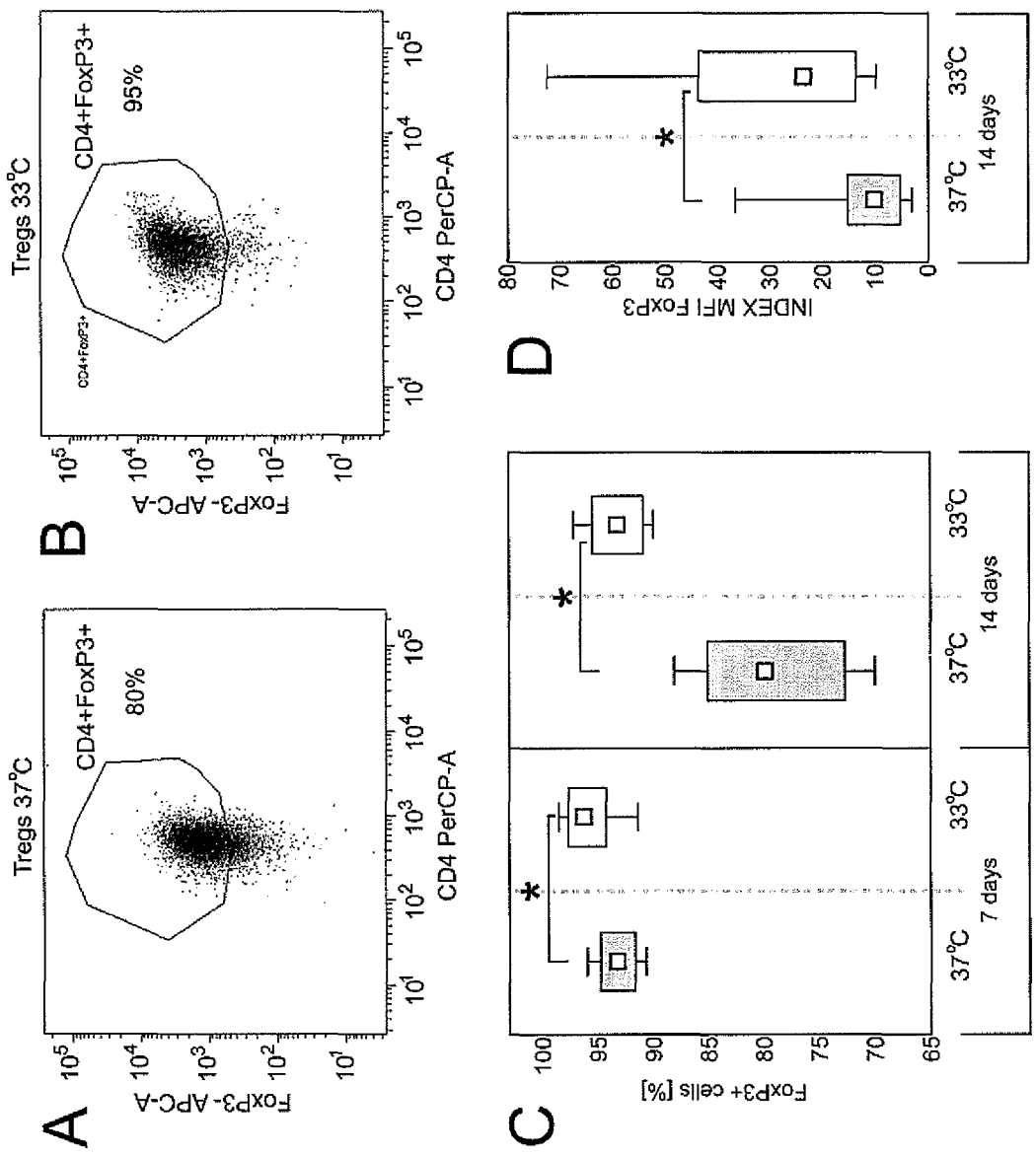
FIG. 2—presents the percentage of CD4$^+$FoxP3$^+$ cells and the intensity of FoxP3 expression in these cells. The upper panel shows dot plots depicting FoxP3 expression in Tregs from the same donor expanded simultaneously at 37° C. (A) and 33° C. (B) for 14 days. The lower panel depicts frequency of CD4$^+$FoxP3$^+$ cells on day 7 and 14 of the culture at two different temperature conditions (37° C. and 33° C., C, n=8) and the intensity of FoxP3 expression in these cells on day 14 (D; n=8). The intensity of FoxP3 expression is expressed as a ratio of median fluorescence intensity (MFI) of the positive signal to median intensity of autofluorescence of unlabeled cells (INDEX MFI FoxP3). The grey and white bars represent the results obtained for the cells expanded at 37° C. and 33° C., respectively. The differences were calculated with Mann-Whitney test for non-parametric data. The values are shown as median, minimum and maximum. An asterisk indicates statistical significance (p<0.05).

It was observed that the Tregs cultured at 33° C. were characterized by significantly higher percentage of FoxP3$^+$ cells on day 7 (p=0.049) and 14 (p=1×10$^{-4}$) as compared with those at standard temperature of 37° C. The difference was more pronounced on the last day of the culture. In addition, on day 14 of expansion, FoxP3$^+$ Tregs expanded at 33° C. showed a higher intensity of FoxP3 expression (p=0.037) measured as a ratio of median fluorescence intensity (MFI) of the positive signal to median autofluorescence intensity of unlabeled cells (INDEX MFI FoxP3; FIG. 2).

Figure 3:
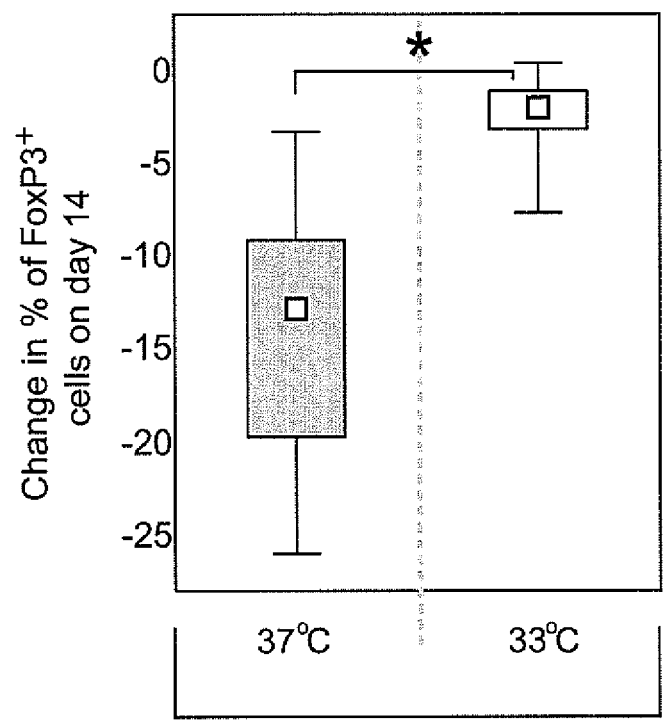
FIG. 3—presents the stability of FoxP3 expression in the entire Treg population. The figure illustrates the difference between the percentage of CD4$^+$FoxP3$^+$ Tregs on day 14 and 7 of the culture at temperature of 37° C. (grey bar; n=8) and 33° C. (white bar; n=8). A significant time-dependent decrease in the percentage of CD4$^+$FoxP3$^+$ cells is observed only for Tregs expanded at 37° C. The cells cultured at 33° C. are characterised by a stable expression of FoxP3 over time. The differences were calculated with Mann-Whitney test for non-parametric data. The values are shown as median, minimum and maximum. An asterisk indicates statistical significance (p<0.05).

When frequency of FoxP3$^+$ Tregs on day 14 was compared with percentage of these cells on day 7 we found that Tregs cultured at 33° C. were characterised by a significantly higher stability of FoxP3 expression during the culture, than those at 37° C. The median decline in percentage of FoxP3$^+$ Tregs at day 14 of the culture was equal to 2% and 12.9% (>6-fold greater) in cultures expanded at 33 and 37° C., respectively (FIG. 3; p=0.001).

Figure 4:
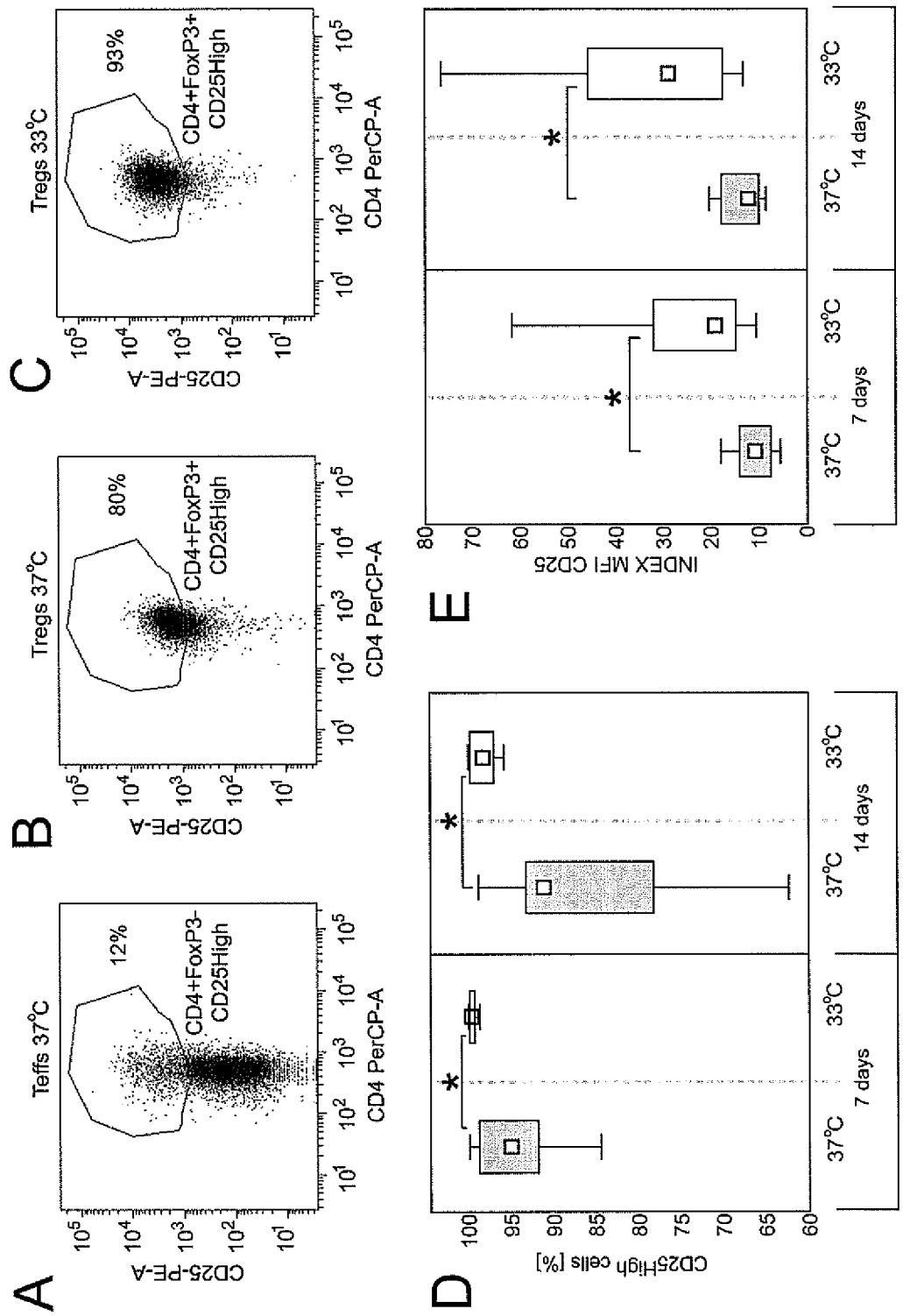
FIG. 4—presents frequency of CD25$^{High}$ cells within CD4$^+$FoxP3$^+$ population and the intensity of CD25 production by these cells on day 7 and 14 of the culture. The upper panel shows dot plots depicting surface expression of CD25 on Teffs after 14 day expansion at 37° C. (A) and on Tregs from the same donor expanded simultaneously at 37° C. (B) and 33° C. (C). The lower panel depicts frequency of CD25$^{High}$ cells within CD4$^+$FoxP3$^+$ Treg population on day 7 and 14 of the culture at two different temperature conditions (37° C. and 33° C., D, n=8) and the intensity of CD25 production by these cells on day 7 and 14 (E; n=8). The intensity of CD25 expression is expressed as a ratio of median fluorescence intensity (MFI) of the positive signal to median intensity of autofluorescence of unlabeled cells (INDEX MFI FoxP3). The grey and white bars represent the results obtained for the cells expanded at 37° C. and 33° C., respectively. The differences were calculated with Mann-Whitney test for non-parametric data. The values are shown as median, minimum and maximum. An asterisk indicates statistical significance (p<0.05).

Similar differences were observed for CD25 molecule expression. A culture at a temperature of 33° C. was associated with a significantly higher percentage of CD25$^{High}$ cells within CD4$^+$FoxP3$^+$ cells on day 7 (p=0.006) and 14 (p=0.003) of expansion. In addition, CD4$^+$FoxP3$^+$CD25$^{High}$ cells cultured at 33° C. were characterized by higher intensity of CD25 expression (INDEX MFI CD25) on day 7 (p=0.014) and 14 (p=0.006) of the culture, than the corresponding cells at of 37° C. (FIG. 4).

Figure 5:
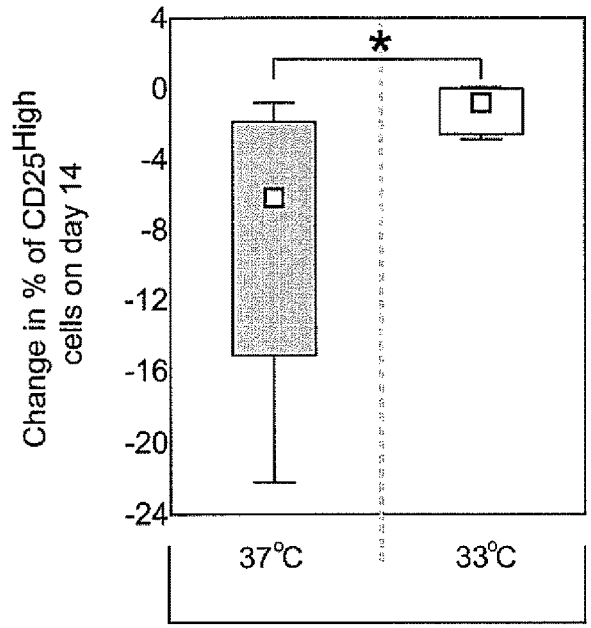
FIG. 5—presents the stability of CD25 expression on CD4$^+$FoxP3$^+$ Tregs. The figure illustrates difference in percentage of CD25$^{High}$ cells within CD4$^+$FoxP3$^+$ Treg population between day 14 and 7 of the culture at temperature of 37° C. (grey bar; n=8) and 33° C., (white bar; n=8). A significant time-dependent decrease in the percentage of CD25$^{High}$ cells is observed only for Tregs expanded at 37° C. The cells cultured at 33° C. are characterised by a high and stable expression of CD25 over time. The differences were calculated with Mann-Whitney test for non-parametric data. The values are shown as median, minimum and maximum. An asterisk indicates statistical significance (p<0.05).
Figure 6:
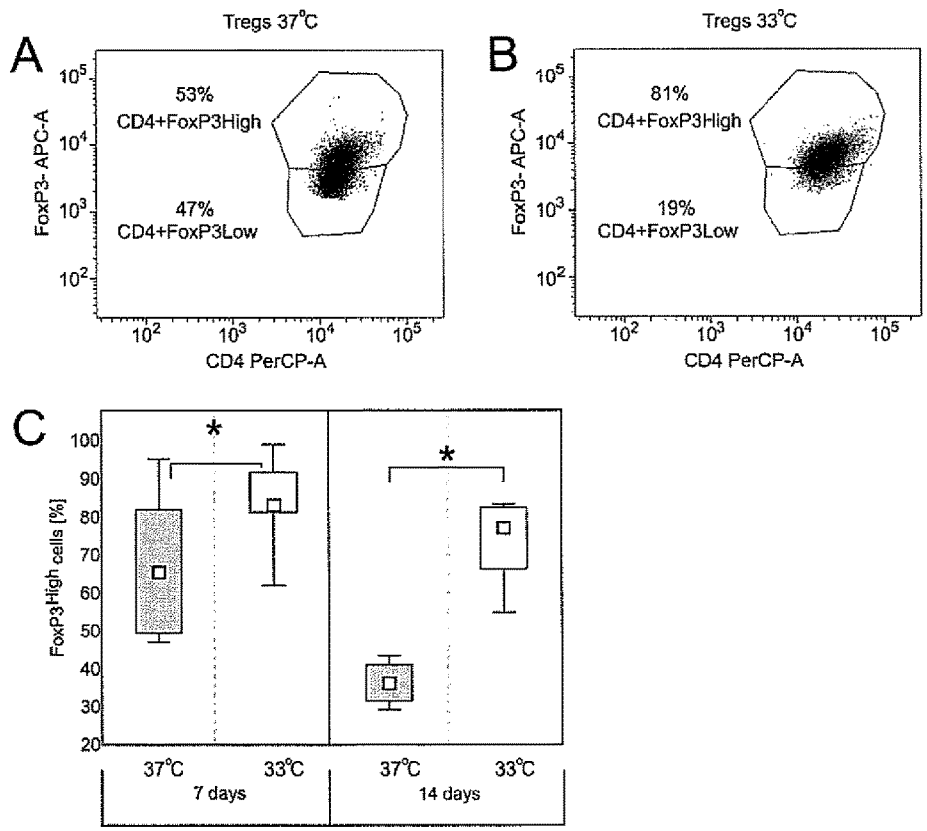
FIG. 6—presents the percentage of CD4$^+$FoxP3$^{High}$ cells. The upper panel shows dot plots depicting frequency of CD4$^+$FoxP3$^{High}$ cells within CD4$^+$FoxP3$^+$ Treg population from the same donor expanded simultaneously at 37° C. (A) and 33° C. (B) for 14 days. The lower panel depicts frequency of CD4$^+$FoxP3$^{High}$ cells on day 7 and 14 of the culture at two different temperature conditions (37° C. and 33° C., C, n=8). The grey and white bars represent the results obtained for the cells expanded at 37° C. and 33° C., respectively. The differences were calculated with Mann-Whitney test for non-parametric data. The values are shown as median, minimum and maximum. An asterisk indicates statistical significance (p<0.05).
Figure 7:
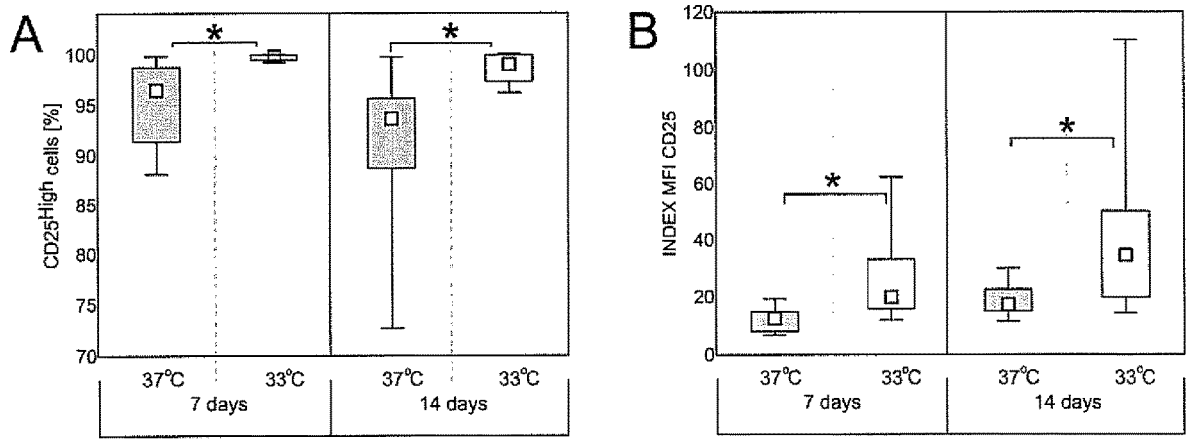
FIG. 7—presents frequency of CD25$^{High}$ cells within CD4$^+$FoxP3$^{High}$ population and the intensity of CD25 production by these cells on day 7 and 14 of the culture. The figure depicts frequency of CD25$^{High}$ cells within CD4$^+$FoxP3$^{High}$ Treg population on day 7 and 14 of the culture at two different temperature conditions (37° C. and 33° C., A, n=8) and the intensity of CD25 production by these cells on day 7 and 14 (B; n=8). The intensity of CD25 expression is expressed as a ratio of median fluorescence intensity (MFI) of the positive signal to median autofluorescence intensity of unlabeled cells (INDEX MFI FoxP3). The grey and white bars represent the results obtained for the cells expanded at 37° C. and 33° C., respectively. The differences were calculated with Mann-Whitney test for non-parametric data. The values are shown as median, minimum and maximum. An asterisk indicates statistical significance (p<0.05).
Figure 8:
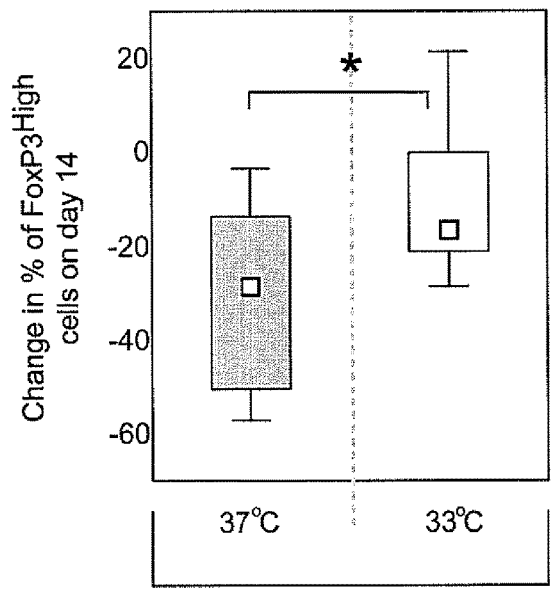
FIG. 8—presents the stability of FoxP3 expression in CD4$^+$FoxP3$^{High}$ Treg population. The figure illustrates the difference between day 14 and 7 of the culture in percentage of CD4$^+$FoxP3$^{High}$ Tregs after expansion at temperature of 37° C. (grey bar; n=8) and 33° C. (white bar; n=8). A significant time-dependent decrease in the percentage of CD4$^+$FoxP3$^{High}$ cells is observed only for Tregs expanded at 37° C. The cells cultured at 33° C. are characterised by significantly more stable expression of FoxP3 over time. The differences were calculated with Mann-Whitney test for non-parametric data. The values are shown as median, minimum and maximum. An asterisk indicates statistical significance (p<0.05).

Likewise, FoxP3, CD25 expression was also more stable in Tregs expanded at 33° C. The median decrease in frequency of CD4$^+$FoxP3$^+$CD25$^{High}$ Tregs at 33° C. on day 14 of the culture was equal to 1.65%, while at 37° C. it was >6-fold higher (6.2%) (FIG. 5). In addition, it was observed that Tregs expanded at 33° C. were characterised by a significantly higher percentage of cells with the highest intensity of FoxP3 expression (FoxP3$^{High}$) on day 7 (p=0.049) and 14 (p=1×10$^{-4}$) of the culture as compared with cells at 37° C. (FIG. 6). Furthermore, CD4$^+$FoxP3$^{High}$ population at 33° C. contained significantly more CD25$^{High}$ cells on day 7 (p=0.002) and 14 (p=0.003) of the culture with higher intensity of CD25 expression (INDEX MFI CD25; day 7 p=0.01; day 14 p=0.049), than the corresponding population at 37° C. (FIG. 7). Like CD4$^+$FoxP3$^+$ cells, CD4$^+$FoxP3$^{High}$ subpopulation was also characterized with higher stability of FoxP3 expression (p=0.037) at 33° C., than at a standard culture temperature (FIG. 8).

Figure 13:
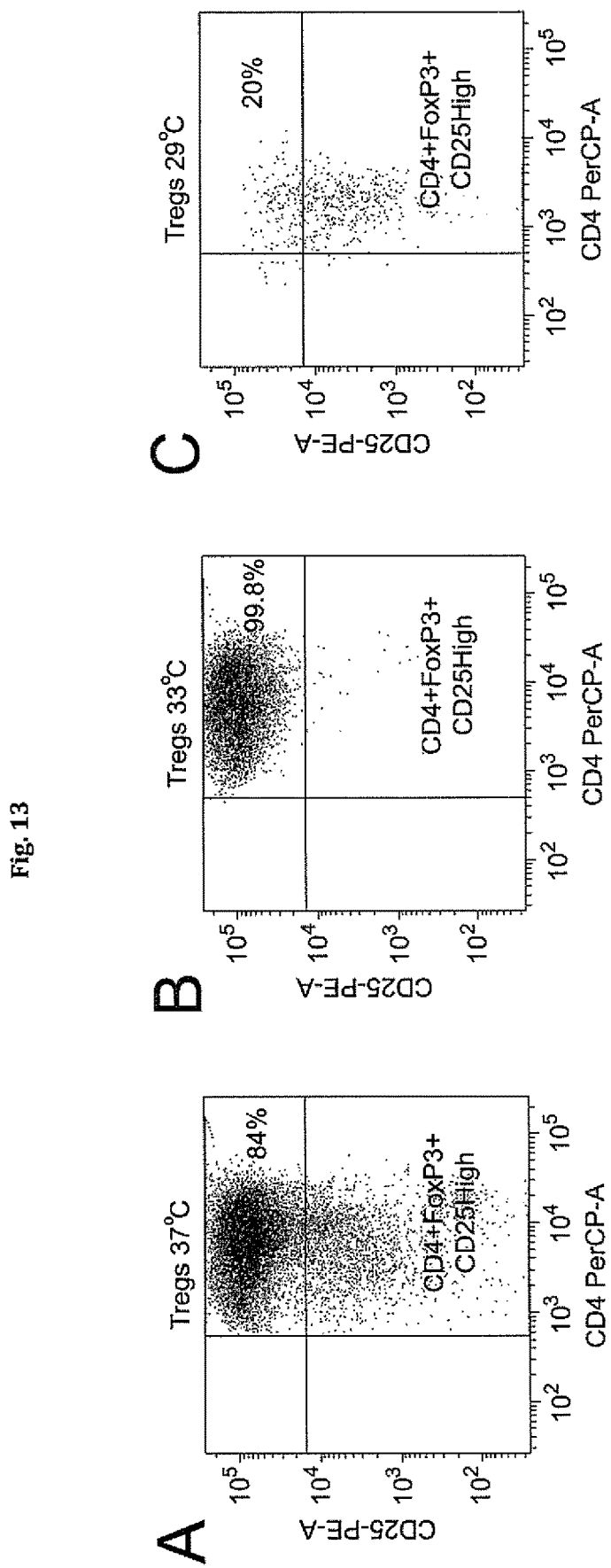
FIG. 13—presents representative dot plots depicting percentage of CD25$^{High}$ cells within CD4$^+$FoxP3$^+$ cells derived from the same donor expanded simultaneously for 14 days at 37° C. (A), 33° C. (B) and 29° C. (C).
Figure 14:
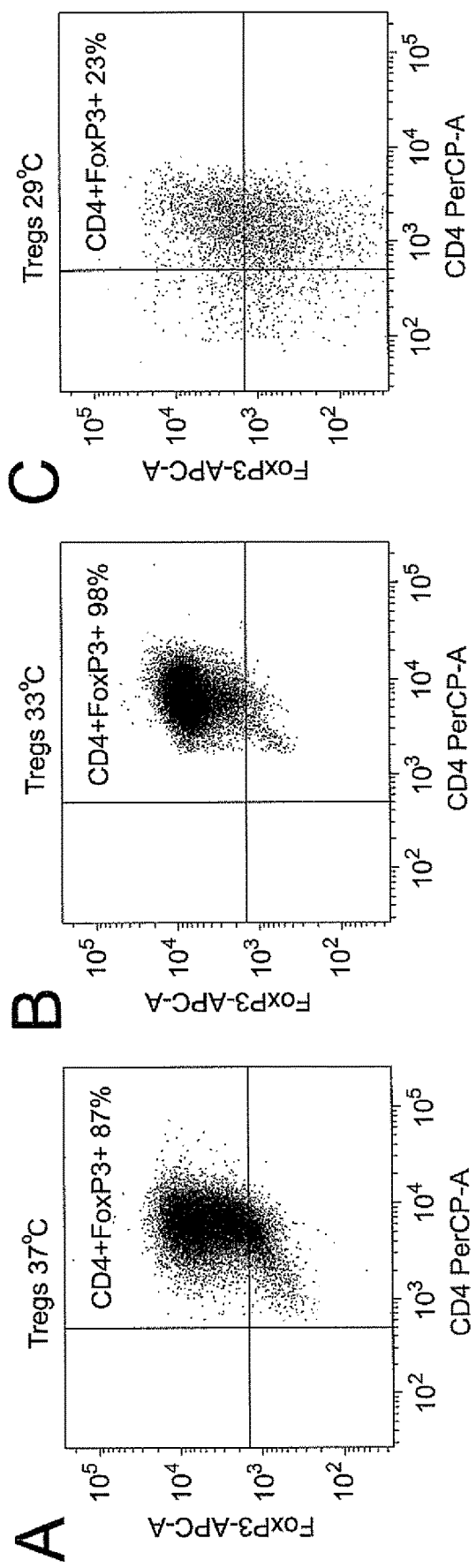
FIG. 14—presents representative dot plots depicting percentage of CD4$^+$FoxP3$^+$ cells within Treg cultures derived from the same donor expanded simultaneously for 14 days at 37° C. (A), 33° C. (B) and 29° C. (C).

As compared to the cells expanded at both 33° C. and 37° C., Tregs cultured at 29° C. were characterised by a rapid loss of characteristic Treg phenotype after the 7$^{th}$ day of expansion. On day 14 of the culture at 29° C. only 7-20% of Tregs remained CD25$^{High}$ cells (FIG. 13). Lowering culture temperature to 29° C. also impaired expression of FoxP3. Even though, after the first 7 days of the culture at 29° C. Tregs showed a relatively high expression of this marker (≈80% of FoxP3$^+$ cells), the percentage of Fox3$^+$ Tregs on day 14 was merely oscillated around 20% (FIG. 14). Between the first and the second week of the culture at 29° C., approximately 60% of Tregs lost expression of this main marker and regulator of their function. Therefore, our experiments demonstrated that 33° C. is the optimal temperature for Treg culture, and not only intensifies their proliferation but also preserves high quality and stability of Tregs. Further temperature reduction is not recommended, and 29° C. is the lower limit of temperature at which Tregs survive, but at the same time stop to proliferate and rapidly lose their typical phenotypic features.

Test of Inhibition of Teff Proliferation by Tregs

At day 7 of the expansion a proliferation inhibition assay was performed. Teffs were stained with 2 μM Violet Proliferation Dye 450 (VPD-450; BD Horizon) for 15 min. at 37° C. and mixed with unstained Tregs expanded at 37 and 33° C. in the following proportions: 2:1, 1:1, 1:½, 1:¼, and 1:⅛. Cells were cocultured for the next 4 days at 37° C. in SCGM medium supplemented with 10% human inactivated AB serum and expanding beads in a 1:1 Teff:bead ratio. VPD-450 stained Teffs cultured alone in presence or absence of beads were used as controls. After the stimulation cells were labeled with 7-amino-actinomycin D (7-AAD, BD Pharmingen) a compound that binds to DNA of dead cells in aim to exclude them from the analysis. The samples were evaluated with flow cytometry (Canto II, BD Biosciences).

Data were analyzed as % of inhibition of Teff proliferation. Each time proliferation of unstimulated Teffs cultured without Tregs (K) was treated as a background and subtracted from % of dividing Teffs in all tested Teff:Treg proportions. Thus % of inhibition of Teff proliferation for K is always equal to 100% and signifies complete inhibition of Teff proliferation. Adequately, results for stimulated Teffs and cultured without Tregs (1:0) are always equal to 0% and correspond to lack of inhibition.

Figure 9:
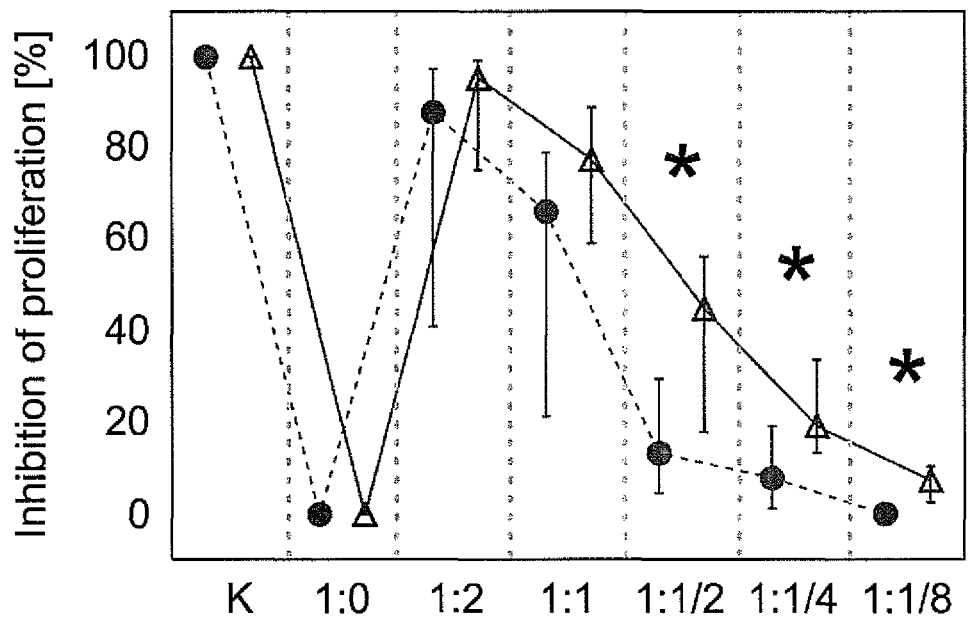
FIG. 9—presents % of inhibition of Teff proliferation by Tregs expanded at 37 (black circles, n=5) and 33° C. (red triangles, n=5). Results for various Teff:Treg ratios are shown. All data were processed in the same way and each time proliferation of unstimulated Teffs cultured without Tregs (K) was treated as a background and subtracted from % of dividing Teffs in all tested Teff:Treg proportions. Thus % of inhibition of Teff proliferation for K is always equal to 100% and signifies complete inhibition of Teff proliferation. Adequately, results for stimulated Teffs and cultured without Tregs (1:0) are always equal to 0% and correspond to lack of inhibition of proliferation. The differences were calculated with Mann-Whitney test for non-parametric data. The values are shown as median, minimum and maximum. An asterisk indicates statistical significance (p<0.05).

Tregs cultured at 33° C. were found to suppress proliferation of Teffs more efficiently, than those expanded at 37° C. The effect was more pronounced for lower Treg:Teff ratios: ½:1, ¼:1 and ⅛:1 (Mann-Whitney U test, p=0.03, p=0.03 and p=0.02, respectively; FIG. 9). All tests were performed at 37° C. that is considered a physiological temperature of human body.

Functional tests for Tregs expanded at 29° C. could not be performed because of the complete inhibition of proliferation and thus cell number was insufficient for concomitant phenotype control and assessment of suppressor activity.

IFN-δ Inhibition Assay and Measurement of IFN-γ Production by Tregs

After 11 days, samples of Tregs expanded at 33° C. and 37° C., were collected for assessment of their inhibitory effect on IFN-γ production (a proinflammatory cytokine) by autologous $CD4^+$ Teffs. Simultaneously, a sample of Teffs expanded, at 37° C. in the same culture medium as the tested Tregs was also harvested. Before the test cells were washed and beads were removed. Then, cells were kept without beads and IL-2 for 48 h in aim to make them resting.

After the next 2 days, i.e. on day 13 of the culture, the cells were washed with PBS and counted. Then, Teffs were stained with a solution of carboxyfluorescein diacetate succinimidyl ester (CFDA; Vybrant® CFDA SE Cell Tracer Kit, Invitrogen; 5 µM; 15 min., 37° C.) in order to discriminate them from unstained Tregs. Subsequently, CFDA-labelled autologous Teffs were mixed in the following proportions with Tregs previously cultured at 33° C. and 37° C.: 1:1, 1:½, 1:¼ and 1:⅛, where number of Teffs was constant and the number of Tregs was variable. The cells were suspended in a fresh culture medium supplemented with human inactivated AB serum (10%), IL-2 (100 U/ml) and monoenzin, a protein transport inhibitor (GolgiStop, BD Biosciences; 2 µl/1000 µl of medium) in aim to inhibit the release of IFN-γ outside the cells. Then, beads coated with anti-CD3 and anti-CD28 antibodies were added in 1:1 Teff:bead ratio. In addition, each time, a positive and negative controls were performed, and IFN-γ production by Tregs cultured without Teffs was also analysed. Positive and negative controls were stimulated and unstimulated Teffs incubated without Tregs, respectively. After 24 h of stimulation at 37° C. (on day 14 day of the culture) the cells were labelled with anti-CD4 and anti-IFN-γ antibodies using a kit for intracellular antigen staining (BD Cytofix/Cytoperm Plus Fixation/Permeabilization Solution Kit with BD GolgiStop; BD Biosciences) and analysed with flow cytometer (Canto II, BD Biosciences).

All the functional tests were conducted at the standard temperature for T cell culture, i.e. 37° C. This temperature was chosen for functional tests because it is a physiological temperature of human body, and ex vivo expanded Tregs will have to function at this temperature after administration to the patient. Data were analyzed as % of inhibition of IFN-γ production by Teffs. Each time IFN-γ production by unstimulated Teffs cultured without Tregs (K) was treated as a background and subtracted from % of IFN-$γ^+$ Teffs in all tested Teff:Treg proportions. Thus, % of inhibition of IFN-γ production by Teffs for K was always equal to 100% and signified complete lack of IFN-γ synthesis. Adequately, results for stimulated Teffs and cultured without Tregs (1:0) were always equal to 0% (lack of inhibition).

Figure 10:
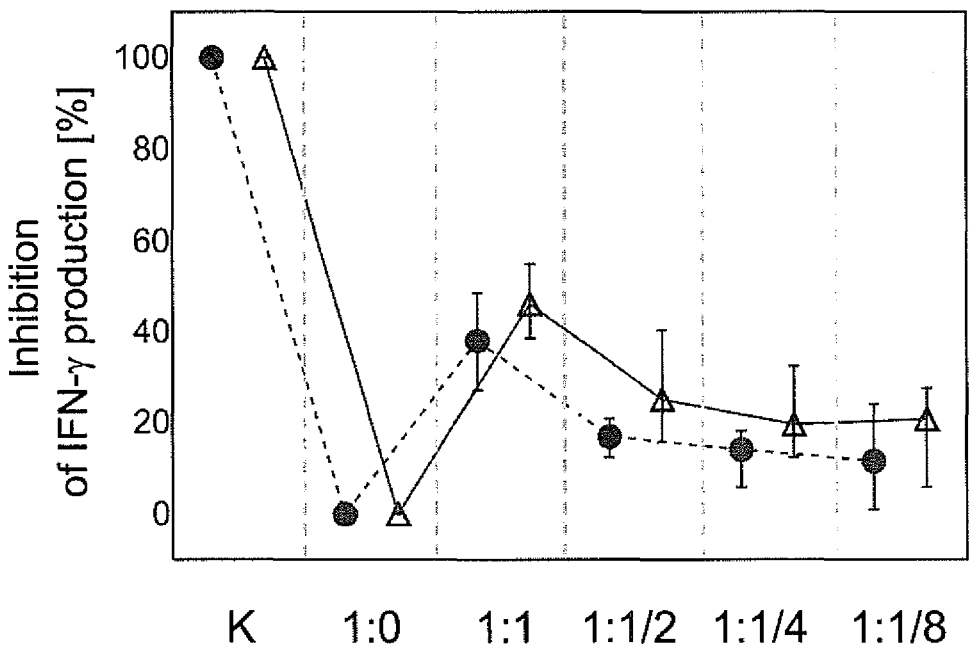
FIG. 10—presents % of inhibition of IFN-γ synthesis in Teffs by Tregs expanded at 37 (gray circles) and 33° C. (red triangles, n=4) for 14 days. Results for various Teff:Treg ratios are shown. All data were processed in the same way and each time IFN-γ production by unstimulated Teffs cultured without Tregs (K) was treated as a background and subtracted from % of IFN-γ$^+$ Teffs in all tested Teff:Treg proportions. Thus, % of inhibition of IFN-γ production by Teffs for K is always equal to 100% and signifies that 100% of Teffs did not synthesize IFN-γ (100% of inhibition). Adequately, results for stimulated Teffs and cultured without Tregs (1:0) are always equal to 0% and correspond to lack of inhibition of IFN-γ production. The differences were calculated with Mann-Whitney test for non-parametric data. The values are shown as median, minimum and maximum.

It was observed that the Tregs previously cultured at 33° C. showed a tendency towards stronger inhibition of IFN-γ production by Teffs, as compared with Tregs expanded at 37° C. (FIG. 10). However, these differences did not reach statistical significance.

Figure 11:
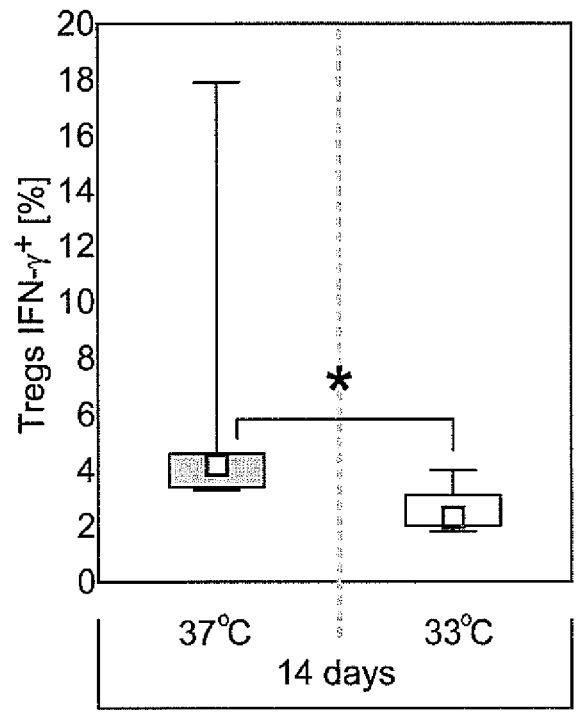
FIG. 11—presents IFN-γ production by Tregs at day 14 of the culture. The figure depicts percentage of IFN-γ* Tregs after 14-day expansion at temperature of 37° C. (grey bar; n=4) and 33° C. (white bar; n=4). The differences were calculated with Mann-Whitney test for non-parametric data. The values are shown as median, minimum and maximum. An asterisk indicates statistical significance (p<0.05).

In addition, it was found that Tregs cultured 33° C. produced only traceable amounts of IFN-γ after 14-day expansion (median 2.5%), while the percentage of IFN-$γ^+$ cells was >2-fold higher in Treg population expanded at 37° C. (5.3% median, p=0.031; FIG. 11). Because of insufficient number of Tregs cultured at 29° C., these tests could not be performed for these cells.

DNA Methylation of the Treg-Specific Demethylated Region (TSDR)

Genomic DNA from 7-day and 14-day cultures of Teffs, Tregs37 and Tregs33 was extracted with the QIAamp DNA blood mini kit (Qiagen, Hilden, Germany). A minimum of 60 ng bisulfite-treated (EpiTect; Qiagen) genomic DNA was used in a real-time PCR to quantify the Foxp3 Treg-specific demethylated region (TSDR). Real-time PCR was performed in a final reaction volume of 20 µl containing 10 µl FastStart universal probe master (Roche Diagnostics, Mannheim, Germany), 50 ng/µl lamda DNA (New England Biolabs, Frankfurt, Germany), 5 pmol/µl methylation or non-methylation-specific probe, 30 pmol/µl methylation or non-methylation-specific primers and 60 ng bisulfite-treated DNA or a respective amount of plasmid standard. The samples were analyzed in triplicates on a ABI 7500 cycler and reported as % of T cells with demethylated TSDR region. Treg samples with extremely low FoxP3 expression (2/13 cultures at 37° C.) were not subjected to this analyses as they were considered not to be the most representative data for this culture condition.

Figure 12:
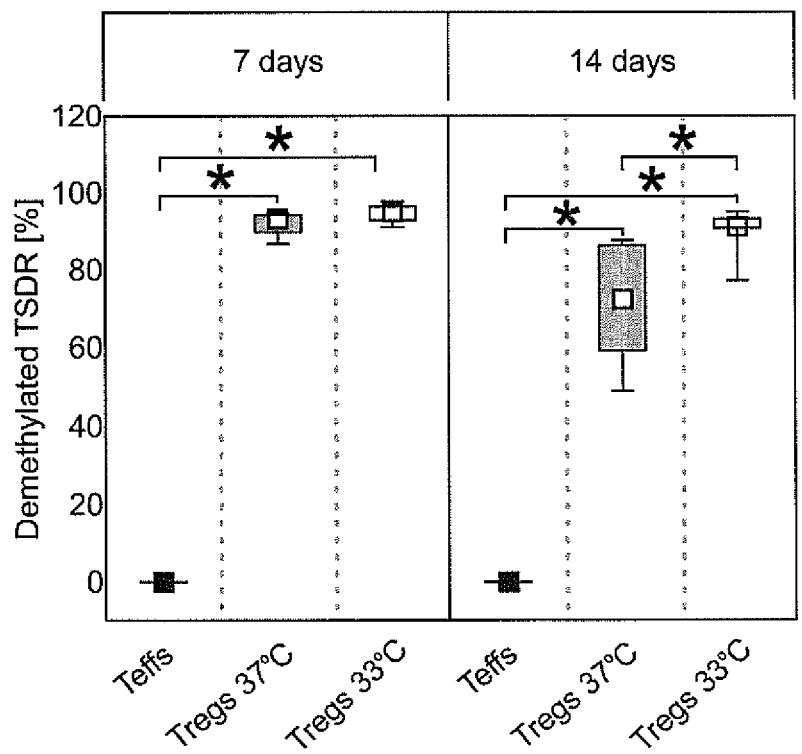
FIG. 12—depicts frequency of cells with demethylated TSDRs within Teff (control samples) and Treg cultures expanded at 37 and 33° C. (black, gray and white symbols, respectively) on day 7 and 14 of expansion (n=5). The differences were calculated with Mann-Whitney test for non-parametric data. The values are shown as median, minimum and maximum. An asterisk indicates statistical significance (p<0.05).

Tregs expanded at 33° C. were characterized by significantly higher frequency of cells with demethylated TSDR after culture in vitro, than those at 37° C. The differences have been escalating with time and reached statistical significance at day 14 (Mann-Whitney U test, p=0.03; FIG. 12). Notably, TSDR demethylation was kept stable over time only in Tregs cultured at 33° C.

REFERENCES

Andrés A (2005). "Cancer incidence after immunosuppressive treatment following kidney transplantation." *Crit Rev Oncol Hematol* 56(1): 71-85.

Barbaro M P, Spanevello A, Palladino G P, Salerno F G, Lacedonia D, Carpagnano G E, (2014). "Exhaled matrix metalloproteinase-9 (MMP-9) in different biological phenotypes of asthma." *Eur J Intern Med* 25(1): 92-96.

Berney T, Secchi A (2009). "Rapamycin in islet transplantation: friend or foe?" *Transpl Int* 22(2): 153-161.

Bluestone J A, Buckner J H, Fitch M, Gitelman S E, Gupta S, Hellerstein M K, Herold K C, Lares A, Lee M R, Li K, Liu W, Long S A, Masiello L M, Nguyen V, Putnam A L, Rieck M, Sayre P H, Tang Q, (2015). "Type 1 diabetes immunotherapy using polyclonal regulatory T cells." *Sci Transl Med* 7(315): 315ra189.

Bluestone J A, Trotta E, Xu D, (2015). "The therapeutic potential of regulatory T cells for the treatment of autoimmune disease." *Expert Opin Ther Targets* 19(8): 1091-1103.

Braza F, Dugast E, Panov I, Paul C, Vogt K, Pallier A, Chesneau M, Baron D, Guerif P, Lei H, Laplaud D A, Volk H D, Degauque N, Giral M, Soulillou J P, Sawitzki B, Brouard S, (2015). "Central role of CD45RA-Foxp3hi memory regulatory T cells in clinical kidney transplantation tolerance." *J Am Soc Nephrol* 26(8): 1795-1805.

Di Ianni M, Falzetti F, Carotti A, Terenzi A, Castellino F, Bonifacio E, Del Papa B, Zei T, Ostini R I, Cecchini D, Aloisi T, Perruccio K, Ruggeri L, Balucani C, Pierini A, Sportoletti P, Aristei C, Falini B, Reisner Y, Velardi A, Aversa F, Martelli M F, (2011). "Tregs prevent GVHD and promote immune reconstitution in HLA-haploidentical transplantation." *Blood* 117(14): 3921-398.

Fontenot J D, Gavin M A, Rudensky A Y, (2003). "Foxp3 programs the development and function of CD4+CD25+ regulatory T cells." *Nat Immunol* 4(4): 330-336.

Gambineri E, Torgerson T R, Ochs H D, (2003). "Immune dysregulation, polyendocrinopathy, enteropathy, and X-linked inheritance (IPEX), a syndrome of systemic autoimmunity caused by mutations of FOXP3, a critical regulator of T-cell homeostasis." *Curr Opin Rheumatol* 15: 430-435.

Gupta S, (2012). "Immunotherapies in diabetes mellitus type 1." *Med Clin North Am* 96(3): 621-634.

Hoffmann P, Boeld T J, Eder R, Huehn J, Floess S, Wieczorek G, Olek S, Dietmaier W, Andreesen R, Edinger M, (2009). "Loss of FOXP3 expression in natural human CD4+CD25+ regulatory T cells upon repetitive in vitro stimulation." *Eur J Immunol* 39(4): 1088-1097.

Kehrmann J, Tatura R, Zeschnigk M, Probst-Kepper M, Geffers R, Steinmann J, Buer J, (2014). "Impact of 5-aza-2'-deoxycytidine and epigallocatechin-3-gallate for induction of human regulatory T cells." *Immunology* 142(3): 384-395.

Lima X T, Cintra M L, Piaza A C, Mamoni R L, Oliveira R T, Magalhães R F, Blotta M H, (2015). "Frequency and characteristics of circulating CD4(+) CD28(null) T cells in patients with psoriasis." *Br J Dermatol* 173(4): 998-1005.

Malek T R (2003). "The main function of IL-2 is to promote the development of T regulatory cells." *J Leukoc Biol* 74(6): 961-965.

Malek T R, Castro I (2010). "Interleukin-2 receptor signaling: at the interface between tolerance and immunity." *Immunity* 33(2): 153-165.

Marek-Trzonkowska N, Mysliwiec M, Dobyszuk A, Grabowska M, Techmanska I, Juscinska J, Wujtewicz M A, Witkowski P, Mlynarski W, Balcerska A, Mysliwska J, Trzonkowski P, (2012). "Administration of CD4+CD25highCD127-regulatory T cells preserves β-cell function in type 1 diabetes in children." *Diabetes Care* 35(9): 1817-1820.

Marek-Trzonkowska N, Myśliwiec M, Siebert J, Trzonkowski P, (2013). "Clinical application of regulatory T cells in type 1 diabetes." *Pediatr Diabetes* 14(5): 322-332.

Marek-Trzonkowska N, Myśliwiec M, Dobyszuk A, Grabowska M, Derkowska I, Juścińska J, Owczuk R, Szadkowska A, Witkowski P, Młynarski W, Jarosz-Chobot P, Bossowski A, Siebert J, Trzonkowski P, (2014). "Therapy of type 1 diabetes with CD4(+) CD25(high)CD127-regulatory T cells prolongs survival of pancreatic islets—results of one year follow-up." *Clin Immunol* 153(1): 23-30.

Marek N, Bieniaszewska M, Krzystyniak A, Juścińska J, Myśliwska J, Witkowski P, Hellmann A, Trzonkowski P, (2011). "The time is crucial for ex vivo expansion of T regulatory cells for therapy." *Cell Transplant* 20(11-12): 1747-1758.

Martelli M F, Di Ianni M, Ruggeri L, Falzetti F, Carotti A, Terenzi A, Pierini A, Massei M S, Amico L, Urbani E, Del Papa B, Zei T, Iacucci Ostini R, Cecchini D, Tognellini R, Reisner Y, Aversa F, Falini B, Velardi A, (2014). "HLAhaploidentical transplantation with regulatory and conventional T-cell adoptive immunotherapy prevents acute leukemia relapse." *Blood* 124(4): 638-644.

Mu Q, Zhang H, Luo X M, (2015). "SLE: another autoimmune disorder influenced by microbes and diet?" *Front Immunol* 6(artykuł 608): 1-10.

Orent W, McHenry A R, Rao D A, White C, Klein H U, Bassil R, Srivastava G, Replogle J M, Raj T, Frangieh M, Cimpean M, Cuerdon N, Chibnik L, Khoury S J, Karlson E W, Brenner M B, De Jager P, Bradshaw E M, Elyaman W, (2015). "Rheumatoid arthritis-associated RBPJ polymorphism alters memory CD4+ T cells." *Hum Mol Genet* DOI: 10.1093/hmg/ddv474 (in press).

Panettieri R A, Jr Covar R, Grant E, Hillyer E V, Bacharier L, (2008). "Natural history of asthma: persistence versus progression-does the beginning predict the end?" *J Allergy Clin Immunol* 121(3): 607-613.

Polansky J K, Kretschmer K, Freyer J, Floess S, Garbe A, Baron U, Olek S, Hamann A, von Boehmer H, Huehn J. (2008). "DNA methylation controls Foxp3 gene expression." *Eur J Immunol* 38(6): 1654-1663.

Prókai Á, Csohány R, Sziksz E, Pap D, Balicza-Himer L, Boros S, Magda B, Vannay Á, Kis-Petik K, Fekete A, Peti-Peterdi J, Szabó A J, (2015). "Calcineurin-inhibition results in upregulation of local renin and subsequent vascular endothelial growth factor production in renal collecting ducts." *Transplantation* DOI: 10.1097/TP.0000000000000961 (in press).

Pujol-Autonell I, Ampudia R M, Monge P, Lucas A M, Carrascal J, Verdaguer J, Vives-Pi M, (2013). "Immunotherapy with Tolerogenic Dendritic Cells Alone or in Combination with Rapamycin Does Not Reverse Diabetes in NOD Mice." *ISRN Endocrinol* 2013 (ID 346987): 1-5.

Rama I, Grinyó J M (2010). "Malignancy after renal transplantation: the role of immunosuppression." *Nat Rev Nephrol* 6(9): 511-519.

Ryba M, Marek N, Hak Ł, Rybarczyk-Kapturska K, Myśliwiec M, Trzonkowski P, Myśliwska J, (2011). "Anti-TNF rescue CD4+Foxp3+ regulatory T cells in patients with type 1 diabetes from effects mediated by TNF." *Cytokine* 55(3): 353-361.

Sénécal V, Deblois G, Beauseigle D, Schneider R, Brandenburg J, Newcombe J, Moore C S, Prat A, Antel J, Arbour N, (2015). "Production of IL-27 in multiple sclerosis lesions by astrocytes and myeloid cells: Modulation of local immune responses." *Glia* DOI: 10.1002/glia.22948 (in press).

Tang Q, Bluestone J A (2013). "Regulatory T-cell therapy in transplantation-moving to the clinic." *Cold Spring Harb Perspect Med* 3(11): pii: a015552.

Trzonkowski P, Bacchetta R, Battaglia M, Berglund D, Bohnenkamp H R, ten Brinke A, Bushell A, Cools N, Geissler B K, Gregori S, Marieke van Ham S, Hilkens C, Hutchinson J A, Lombardi G, Madrigal J A, Marek-Trzonkowska N, Martinez-Caceres E M, Roncarolo M G, Sanchez-Ramon S, Saudemont A, Sawitzki B, (2015). "Hurdles in therapy with regulatory T cells." *Sci Transl Med* 7(304): 304ps18.

Trzonkowski P, Bieniaszewska M, Juścińska J, Dobyszuk A, Krzystyniak A, Marek N, Myśliwska J, Hellmann A, (2009). "First-in-man clinical results of the treatment of patients with graft versus host disease with human ex vivo expanded CD4+CD25+CD127-T regulatory cells." *Clin Immunol* 133(1): 22-26.

Trzonkowski P, Dukat-Mazurek A, Bieniaszewska M, Marek-Trzonkowska N, Dobyszuk A, Juścińska J, Dutka M, Myśliwska J, Hellmann A, (2013). "Treatment of graft-versus-host disease with naturally occurring T regulatory cells." *BioDrugs* 27(6): 605-614.

Trzonkowski P, Szaryńska M, Myśliwska J, Myśliwski A, (2009). "Ex vivo expansion of CD4(+)CD25(+) T regulatory cells for immunosuppressive therapy." *Cytometry A* 75(3): 175-188.

Vignali D A, Collison L W, Workman C J, (2008). "How regulatory T cells work." *Nat Rev Immunol* 8(7): 523-532.

Wang Y M, Zhang G Y, Wang Y, Hu M, Wu H, Watson D, Hori S, Alexander I E, Harris D C, Alexander S I, (2006). "Foxp3-transduced polyclonal regulatory T cells protect against chronic renal injury from adriamycin." *J Am Soc Nephrol* 17(3): 697-706.

Yi S, Ji M, Wu j, Ma X, Phillips P, Hawthorne W J, O'Connell P J, (2012). "Adoptive transfer with in vitro expanded human regulatory T cells protects against porcine islet xenograft rejection via interleukin-10 in humanized mice." *Diabetes* 61(5): 1180-1191.

Zhang N, Su D, Qu S, Tse T, Bottino R, Balamurugan A N, Xu J, Bromberg J S, Dong H H, (2006). "Sirolimus is associated with reduced islet engraftment and impaired beta-cell function." *Diabetes* 55(9): 2429-2436.

Zhao K, Ruan S, Yin L, Zhao D, Chen C, Pan B, Zeng L, Li Z, Xu K, (2015). "Dynamic regulation of effector IFN-γ-producing and IL-17-producing T cell subsets in the development of acute graft-versus-host disease." *Mol Med Rep* DOI: 10.3892/mmr.2015.4638 (in press).

The invention claimed is:

1. A method for in vitro expansion of $CD4^+CD25^{High}CD127^{-/low}FoxP3^+$ regulatory T cells (Tregs), said method comprising:
    expanding said Tregs, wherein Treg expansion takes place at 33° C. for at least 14 days in a culture; and
    adding magnetic beads coated with anti-CD3 and anti-CD28 antibodies at a 1:1 cell:bead ratio and interleukin-2 to the culture.

2. The method of claim 1, wherein the expanded Tregs are used for clinical therapies of adverse immune reactions.

3. The method of claim 2, wherein the adverse immune reactions are selected from the group consisting of autoimmune diseases, transplant rejection, allergic reactions, graft rejection, and graft-versus-host disease.

4. The method of claim 1, wherein the Tregs are polyclonal or antigen-specific cells.

5. The method of claim 1, wherein the Treg expansion provides about 300% more Tregs after a 14-day culture in vitro as compared to an expansion method that takes place at a temperature of 37° C.

\* \* \* \* \*